United States Patent [19]

Mine et al.

[11] Patent Number: 4,666,889

[45] Date of Patent: May 19, 1987

[54] METHOD FOR COMBATTING VIRAL INFECTIONS

[75] Inventors: Yasuhiro Mine, Toyono; Yoshiko Yokota, Ibaraki, both of Japan

[73] Assignee: Fujisawa Pharmaceutical Co., Ltd., Osaka, Japan

[21] Appl. No.: 669,078

[22] Filed: Nov. 7, 1984

[30] Foreign Application Priority Data

Nov. 10, 1983 [JP]   Japan .................................. 58-211738

[51] Int. Cl.$^4$ ............................................. A61K 37/02
[52] U.S. Cl. .................................................... 514/18
[58] Field of Search ..................... 260/112.5 R; 514/18

[56] References Cited

U.S. PATENT DOCUMENTS 4,322,341   3/1982   Kitaura et al. ............... 260/112.5 R

FOREIGN PATENT DOCUMENTS 59-76021   4/1984   Japan ..................................... 514/18

OTHER PUBLICATIONS

Fujisawa Pharm KK, JP 186642, 1982 (Abstract in English).

Primary Examiner—Donald B. Moyer
Assistant Examiner—F. T. Moezie
Attorney, Agent, or Firm—Oblon, Fisher, Spivak, McClelland & Maier

[57] ABSTRACT

This invention relates to a method for combatting viral infections in a mammal comprising administering to the mammal an acylpeptide of the formula

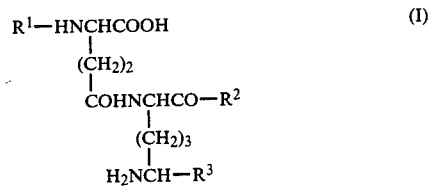

wherein $R^1$ is lactoyl-alanyl, $R^2$ is carboxymethylamino and $R^3$ is carboxy; or $R^1$ is heptanoyl, $R^2$ is 1-carboxyethylamino and $R^3$ is carboxy; or $R^1$ is stearoyl, $R^2$ is 1-carboxyethylamino and $R^3$ is hydrogen; or $R^1$ is octanoyl, $R^2$ is 1-carboxyethylamino and $R^3$ is hydrogen.

4 Claims, No Drawings

METHOD FOR COMBATTING VIRAL INFECTIONS

BACKGROUND OF THE INVENTION

1. Field of the Invention

This invention relates to a pharmaceutical composition for combatting viral infections and a method of using the composition thereof for treating viral infections. More particularly, this invention relates to a pharmaceutical composition for combatting viral infections comprising, as an active ingredient, an acylpeptide or its pharmaceutically acceptable salt, and to a method of use of the acylpeptide or its pharmaceutically acceptable salt for prophylaxis or therapentic treatment of infectious disease caused by viral in human beings or animals.

2. Description of the Prior Art

The acylpeptide to be used as the active ingredient in the pharmaceutical composition for combatting viral infections according to this invention is represented by the following formula (I):

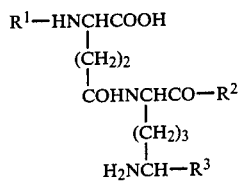

wherein $R^1$ is lactoyl-alanyl, $R^2$ is carboxymethylamino and $R^3$ is carboxy; or $R^1$ is heptanoyl, $R^2$ is 1-carboxyethylamino and $R^3$ is carboxy; or $R^1$ is stearoyl, $R^2$ is 1-carboxyethylamino and $R^3$ is hydrogen; or $R^1$ is octanoyl, $R^2$ is 1-carboxyethylamino and $R^3$ is hydrogen.

The acylpeptide of the above general formula (I) and pharmaceutically acceptable salts thereof are known to be compounds having immunopotentiating activity (cf. U.S. Pat. No. 4322341, for example).

The present inventors found that the acylpeptide (I) and pharmaceutically acceptable salts thereof have excellent preventive and therapeutic effects against various viral infections and, as a result of further research based on this new finding, have completed the present invention.

SUMMARY OF THE INVENTION

The pharmaceutically acceptable salt of the acylpeptide (I) to be used as the active ingredient in this invention is, for example, an organic or inorganic salt such as sodium salt, potassium salt, calcium salt, ammonium salt, ethanolamine salt, triethylamine salt, dichlorohexylamine salt, or an acid addition salt with an organic or inorganic acid, such as acetate, trifluoroacetate, lactate, maleate, fumarate, tartrate, citrate, methanesulfonate, hydrochloride, sulfate, nitrate or phosphate.

DESCRIPTION OF THE PREFERRED EMBODIMENTS

The acylpeptide (I) includes 1 or 2 or more stereoisomers with respect to asymmetric carbon atoms in the molecule, and all these compounds can also be used as the active ingredient of this invention.

Among the acylpeptide (I) and pharmaceutically acceptable salt thereof to be used as the active ingredient in the practice of this invention, exemplary compounds are as follows:

Compound (1)

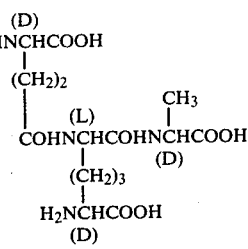

Compound (2)

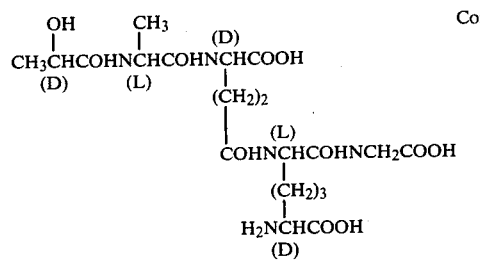

Compound (3)

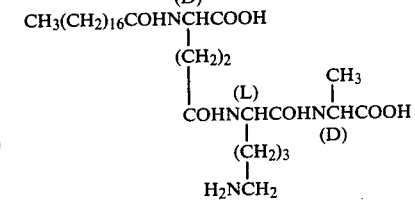

Compound (4)

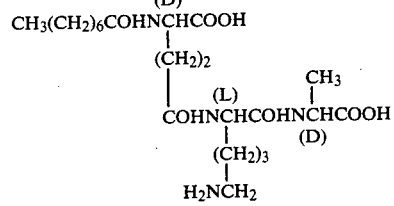

The pharmaceutical composition for combatting viral infections according to this invention can be used in the prophylaxis and treatment of various viral infections in humans and animals.

Such viral infections include viral infections with such viruses as influenza virus, Herpes simplex virus infection and Friend leukemia virus induced splenomegally.

The following test examples are illustrative of the effect of this invention.

EXAMPLES

Test 1

Effect of compound (1) in influenza virus-infected mice:

ICR-strain male mice (4 weeks old) (in groups of 10 individuals) were anesthesized by injection of 0.5% pentobarbital into the caudal vein and then inoculated intranasally with 0.025 ml/mouse of a $10^5$-fold dilution of influenza virus APR/8 ($EID_{50}$: $6 \times 10^2$), to thereby cause infection therewith. The compound (1) of the invention (in 0.5% aqueous methylcellulose solution) was orally administered in prescribed concentrations 4 times before infection, namely 6 days, 5 days, 4 days and 1 day before infection. In separate groups, the compound (1) was orally administered 3 times after infection, namely 1 day, 2 days and 3 days after infection.

The mice were observed for survival or death for 14 days following infection and the effects were evaluated in terms of survival rate (%).

The results obtained are given in the table which follows.

| Administration of compound (1) | Dose (mg/kg) | Survival rate (%) |
|---|---|---|
| Before infection | 0.01 | 28.6* |
|  | 1 | 40.0 |
| After infection | 0.01 | 20.0 |
|  | 1 | 60.0 |
| Control | 0 | 0 |

Note:
*n = 7.

Test 2

Effects of compounds (1) and (2) in herpes simplex virus-infected mice:

ICR-strain male mice (4 weeks old) (in groups of 10 individuals) were intraperitoneally inoculated with $1.0 \times 10^3$ pfu/mouse of herpes simplex type 1 virus (Miyama strain) to thereby cause infection therewith. Prescribed amounts of compounds (1) and (2) (each in aqueous solution) were respectively administered to the mice subcutaneously 1 day, 2 days, 3 days and 4 days after infection. In separate groups, prescribed amounts of the compound (1) (in 0.5% aqueous methylcellulose solution) were orally administered 1 day, 2 days, 3 days and 4 days after infection.

The mice were observed for survival or death for 14 days following infection and the effects were evaluated in terms of survival rate (%).

The results obtained are given in the following table.

|  | Dose (mg/kg) | Survival rate (%) |
|---|---|---|
| Compound (1) (given subcutaneously) | 0.1 | 40 |
|  | 1 | 90 |
| Compound (1) (given orally) | 0.1 | 50 |
|  | 1 | 60 |
| Compound (2) (given subcutaneously) | 0.1 | 40 |
|  | 1 | 60 |
| Control | 0 | 0 |

Test 3

Effects of compounds (3) and (4) in herpes simplex virus-infected mice:

ICR-strain male mice (4 weeks old) (in groups of 20 individuals) were inoculated intraperitoneally with $1.0 \times 10^5$ pfu/mice of herpes simplex type 1 virus (Miyama strain) to thereby cause infection therewith. Prescribed amounts of compounds (3) and (4) were administered to the mice orally (in 0.5% aqueous methylcellulose solution) or subcutaneously (in aqueous solution) 6 days, 5 days, 2 days and 1 day before infection and orally or subcutaneously, respectively, 1 day and 2 days after infection.

The mice were observed for survival or death for 20 days following infection and the effects were evaluated in terms of survival rate (%).

The results obtained are shown in the following table.

| Compound | Dose (mg/kg) | Survival rate (%) Oral | Survival rate (%) Subcutaneous |
|---|---|---|---|
| Compound (3) | 0.01 | 30 | 10 |
|  | 0.1 | 35 | 25 |
|  | 1 | 55 | 20 |
|  | 10 | 75 | 90 |
| Compound (4) | 0.01 | 55 | 35 |
|  | 0.1 | 65 | 35 |
|  | 1 | 80 | 90 |
|  | 10 | 40 | 55 |
| Control | 0 | 20 | 15 |

Test 4

Inhibitory effects of compounds (3) and (4) against Friend leukemia virus-induced splenomegaly:

Male C$_3$H/HeN mice (4 weeks old) (in groups of 10 individuals) were inoculated intraperitoneally with $3.1 \times 10^1$ MID$_{50}$/mouse of Friend leukemia virus to thereby cause infection. Prescribed amounts of the compounds (3) and (4) of the invention (each in aqueous solution) were intraperitoneally administered to the mice according to the schedules given below (Experiments 1 and 2).

(1) Experiment 1:

Administration was performed 6 days, 5 days, 4 days and 1 day before infection.

(2) Experiments 2:

Administration was performed 6 days, 5 days, 4 days and 1 day before infection and 1 day, 2 days and 3 days after infection.

For efficacy evaluation, each mouse was sacrificed by exsanguination 14 days after infection and the spleen weight (mg) was measured.

The results obtained are shown in the table given below. The percent infection inhibition data were calculated using the following formula:

$$\% \text{ Infection inhibition} = \left(1 - \frac{\text{spleen weight of dosed group} - \text{normal spleen weight of uninfected group}}{\text{spleen weight of control group} - \text{normal spleen weight of uninfected group}}\right) \times 100$$

Normal spleen weight in uninfected group (mg): 82±3.0

| Compound | Dose (mg/kg) | Mean spleen weight (mg) | Infection inhibition (%) |
|---|---|---|---|
| (1) Experiment 1 | | | |
| Compound (3) | 10 | 1066 ± 169* | 35.8 |
|  | 1 | 1329 ± 98* | 18.7 |
|  | 0.01 | 1504 ± 74 | 7.2 |
| Compound (4) | 10 | 957 ± 143* | 42.9 |
|  | 1 | 1178 ± 71* | 28.5 |
|  | 0.01 | 1236 ± 59* | 24.7 |
| Control | 0 | 1615 ± 20 |  |
| (2) Experiment 2 | | | |
| Compound (3) | 10 | 1089 ± 167* | 34.6 |
|  | 1 | 1105 ± 102* | 33.3 |
|  | 0.01 | 1146 ± 149* | 30.6 |
| Compound (4) | 10 | 1047 ± 178* | 37.1 |
|  | 1 | 1148 ± 83* | 30.5 |
|  | 0.01 | 1361 ± 112* | 16.5 |

| Compound | Dose (mg/kg) | Mean spleen weight (mg) | Infection inhibition (%) |
|---|---|---|---|
| Control | 0 | 1615 ± 20 | |

Note:
*$p < 0.05$.

Pharmaceutical compositions for combatting viral infections according to this invention can be used in various dosage forms which may for example be solid, semi-solid or liquid preparations containing the active ingredient of this invention in admixture with an organic or inorganic vehicle or excipient suitable for external, oral or parenteral administration. The active ingredient is used in combination with a nontoxic, pharmaceutically acceptable vehicle or carrier which is commonly employed in the production of tablets, pellets, capsules, suppositories, solutions, emulsions, suspensions and so forth. Among the useful vehicles and carriers are water, glucose, lactose, gum arabic, gelatin, mannitol, starch paste, magnesium trisilicate, talc, methylcellulose, polyethylene glycol, corn starch, keratin, colloidal silica, potato starch, urea, and other substances suitable for the production of solid, semi-solid or liquid pharmaceutical preparations. In addition to such a vehicle or carrier, there may also be employed an adjuvant, stabilizer, viscosity builder or thickener, colorant, flavor or/and so forth. The pharmaceutical compositions for combating viral infections may also contain a preservative or/and an antibacterial agent so that the activity of the active ingredient can be preserved. The active ingredient compound is contained in such a pharmaceutical composition in a sufficient amount for the production of desirable therapeutic effects against the progress or actual condition of a disease concerned.

For use in human beings or animals, such a pharmaceutical composition for combating viral infections is desirably administered intravenously, subcutaneously, intramuscularly or orally. While the dosage or therapeutically effective dose of the active ingredient of this invention, namely the acylpeptide (I) or a pharmaceutically acceptable salt thereof, depends on the age and condition of the patient to be treated, it is generally used at a dose level of about 0.01 to 10 mg daily per kilogram body weight of a human being or animal, for therapeutic purposes.

The pharmaceutical composition for combatting viral infections according to this invention may be used in combination with other antiviral drug.

The following examples illustrate this invention.

EXAMPLE 1

| (Tablet) | |
|---|---|
| Compound (1) | 200 mg |
| Mannitol | 400 mg |
| Magnesium stearate | 10 mg |
| Starch | 50 mg |

The above ingredients are made into a tablet by the conventional method.

EXAMPLE 2

| (Capsule) | |
|---|---|
| Compound (2) | 300 mg |
| Magnesium stearate | 15 mg |

The above ingredients are encapsulated by the conventional method.

EXAMPLE 3 (INJECTION)

The composition (1) is aseptically distributed in 100-mg portions into vials, followed by elimination of water and bacteria and tight closure. Just prior to use, 2 ml of 0.5% lidocaine for injection is added to each vial to prepare an injectable solution.

We claim:

1. A method of treatment for combatting influenza viral infection in a mammal comprising administering to a mammal in need of such treatment an acylpeptide of the formula

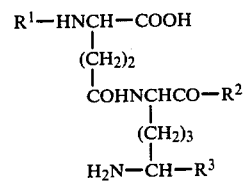

or a pharmaceutically acceptable salt thereof, wherein
$R^1$ is lactoyl-alanyl, $R^2$ is carboxymethylamino and $R^3$ is carboxy;
$R^1$ is heptanoyl, $R^2$ is 1-carboxy-ethylamino and $R^3$ is carboxy;
$R^1$ is stearoyl, $R^2$ is 1-carboxyethylamino and $R^3$ is hydrogen; or
$R^1$ is octanoyl, $R^2$ is 1-carboxyethylamino and $R^3$ is hydrogen in
a pharmaceutically acceptable carrier, in an amount effective to combat the influenza viral infection.

2. A method of treatment for combatting herpes simplex viral infection in a mammal comprising administering to a mammal in need of such treatment an acylpeptide of the formula

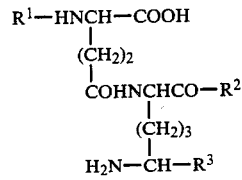

or a pharmaceutically acceptable salt thereof, wherein
$R^1$ is lactoyl-alanyl, $R^2$ is carboxymethylamino and $R^3$ is carboxy;
$R^1$ is heptanoyl, $R^2$ is 1-carboxy-ethylamino and $R^3$ is carboxy;
$R^1$ is stearoyl, $R^2$ is 1-carboxyethylamino and $R^3$ is hydrogen; or
$R^1$ is octanoyl, $R^2$ is 1-carboxyethylamino and $R^3$ is hydrogen and
a pharmaceutically acceptable carrier, in an amount effective to combat the herpes simplex viral infection.

3. The method of treatment according to claim 1 which is a prophylactic treatment.

4. The method of treatment according to claim 2 which is a prophylactic treatment.

* * * * *